United States Patent [19]
Niemi

[11] 4,088,141
[45] May 9, 1978

[54] FAULT CIRCUIT FOR STIMULATOR
[75] Inventor: Bill Howard Niemi, Brooklyn Park, Minn.
[73] Assignee: Stimulation Technology, Inc., Minneapolis, Minn.
[21] Appl. No.: 680,634
[22] Filed: Apr. 27, 1976
[51] Int. Cl.² ............................................ A61N 1/36
[52] U.S. Cl. ................................................. 128/421
[58] Field of Search ............ 128/2.1 P, 2.1 R, 303.13, 128/303.14, 419 R, 419 D, 421, 422, 423 R; 317/9 AC, 31, 50; 361/86, 91

[56] References Cited
U.S. PATENT DOCUMENTS

| | | | |
|---|---|---|---|
| 3,513,353 | 5/1970 | Lansch | 317/31 |
| 3,523,539 | 8/1970 | Lavezzo et al. | 128/422 |
| 3,612,060 | 10/1971 | Colyer | 128/422 |
| 3,860,009 | 1/1975 | Bell et al. | 128/419 D |

FOREIGN PATENT DOCUMENTS
897,961 6/1962 United Kingdom ............ 128/303.14

*Primary Examiner*—William E. Kamm

[57] ABSTRACT

An improved control circuit which may be incorporated into a medical transcutaneous nerve or muscle stimulator for disabling the output from the stimulator to stimulation electrodes connected thereto upon the occurrence of an undesirable output event of the kind which may result in an electrical shock or burn to user of the stimulator. This disablement by the control circuit may be triggered when electrode impedance exceeds a threshold level, or when the current level of the output undergoes excessive change, or when the power source to the unit is interrupted. Included may be visual signaling functions.

8 Claims, 5 Drawing Figures

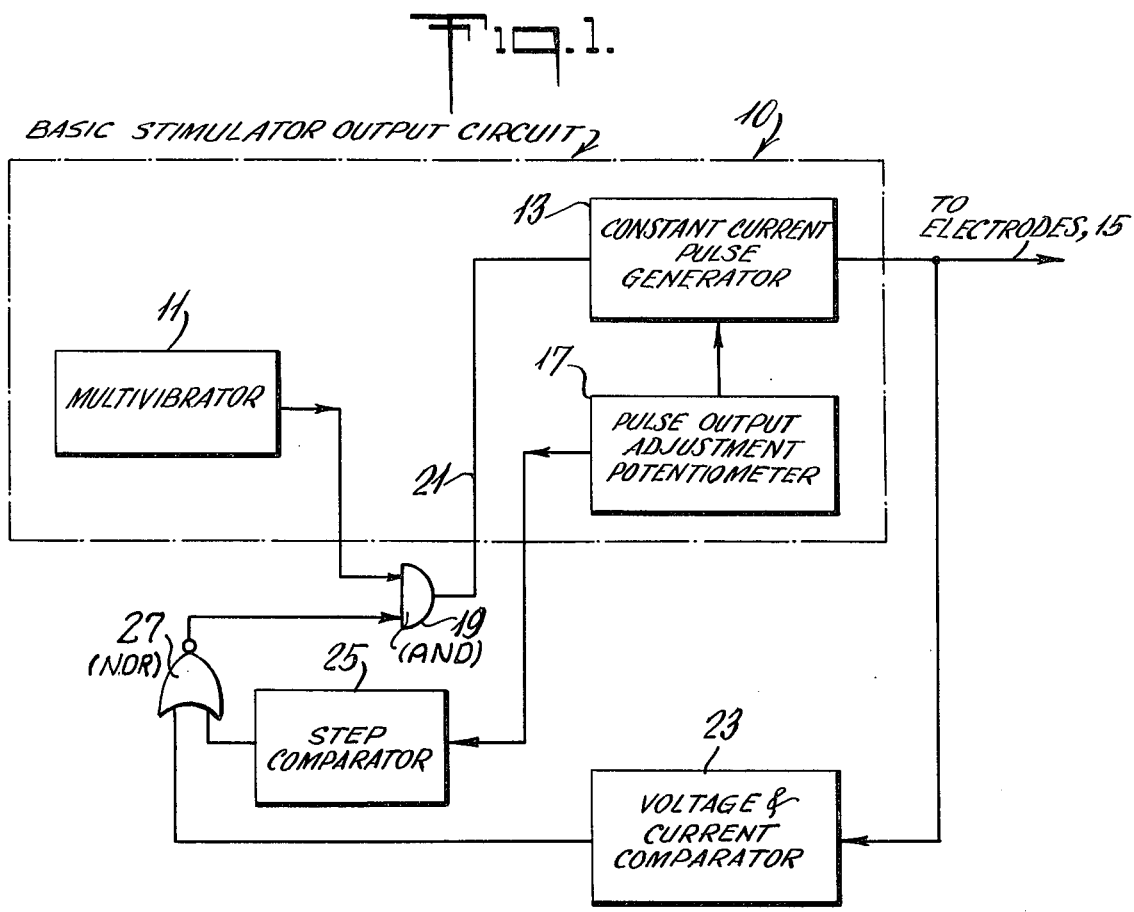
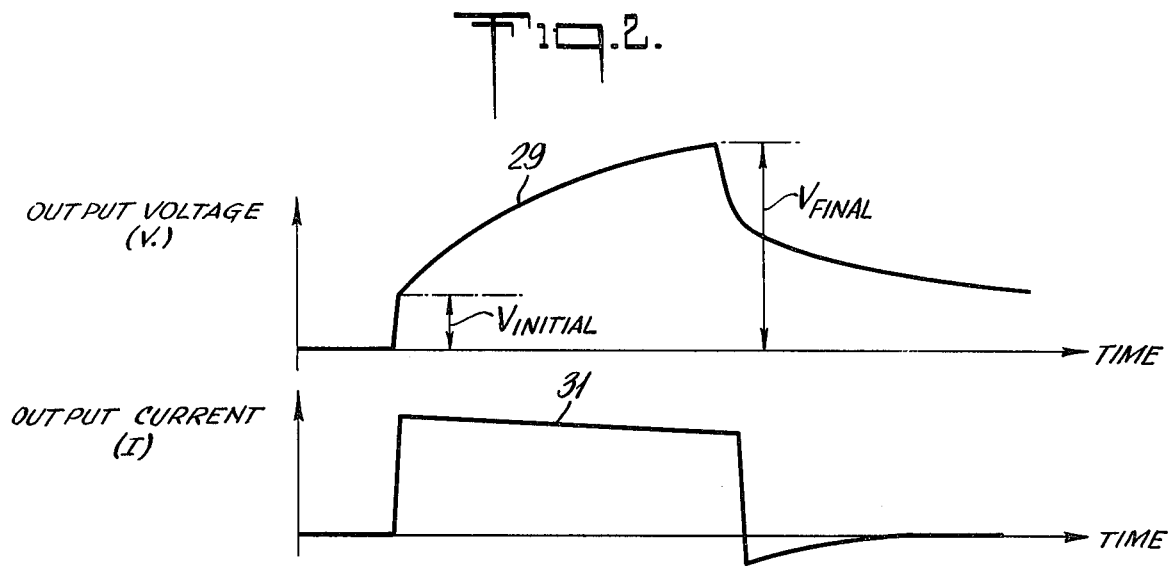

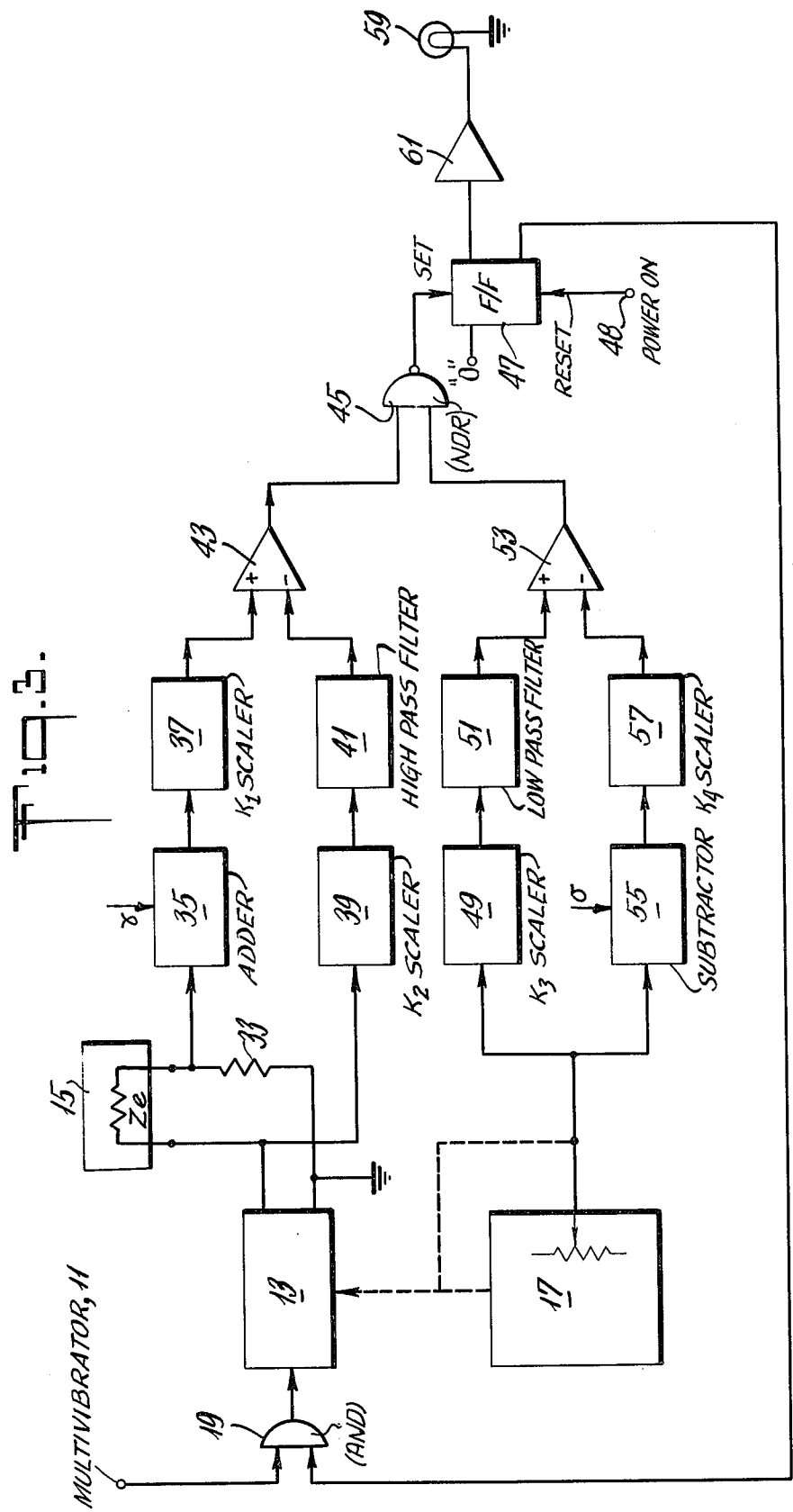

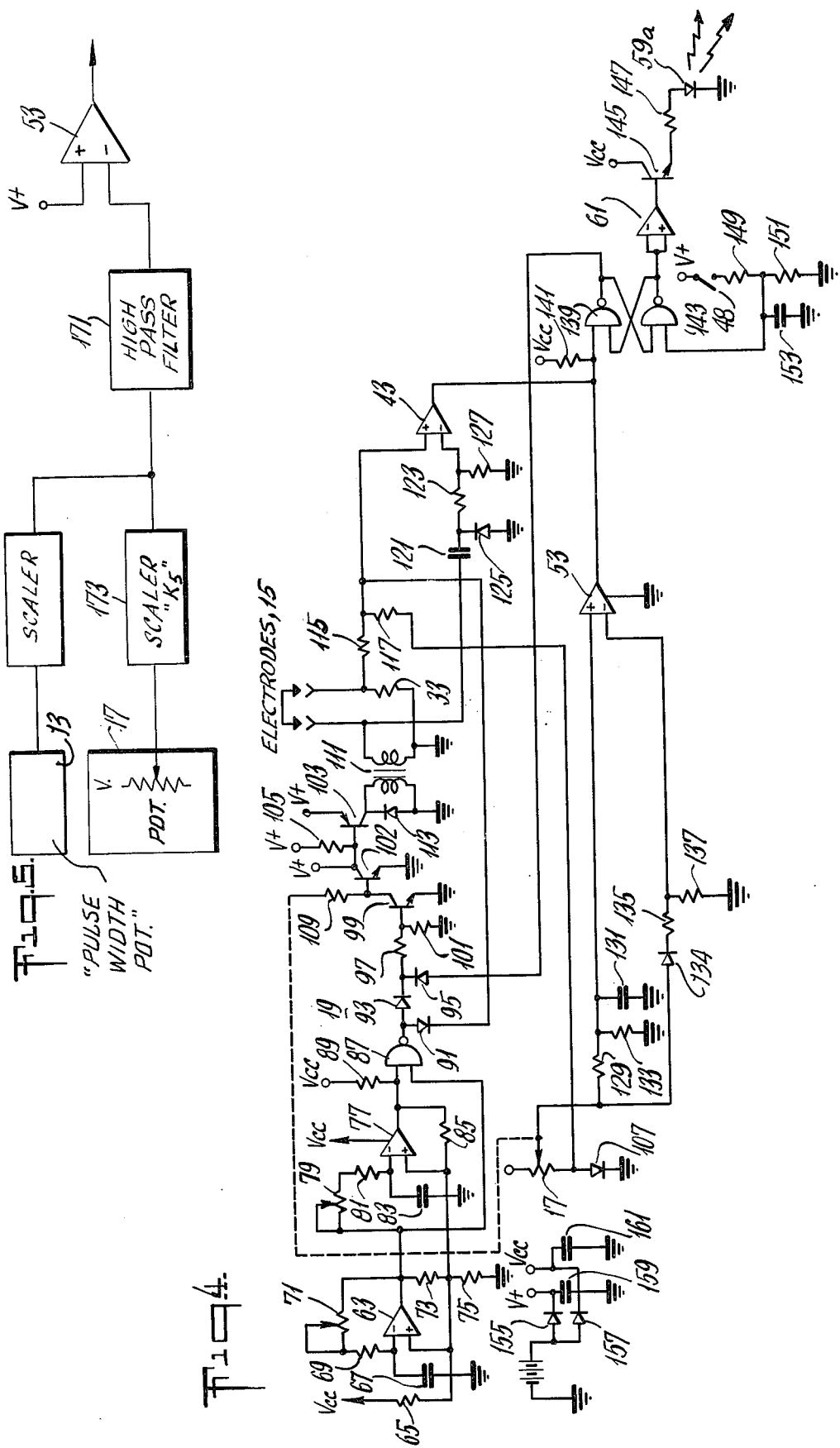

FAULT CIRCUIT FOR STIMULATOR

BACKGROUND OF THE INVENTION

When using transcutaneous nerve stimulators for pain control and body function stimulation, sudden increases in output current to the patient, via the electrodes used with these stimulators, have been known to occur. These surges in output current can result in discomfort, skin burns, muscle spasms, and pain and fright to a patient. With weak or sensitive patients or with patients with cardiac conditions these results can be dangerous or even disastrous.

Often, these sudden increases in output current are the result of intermittent electrode connections, improper unit operation, surges within the unit due to circuitry failures or intermittent power supply connections. These types of surge generating conditions, especially where the stimulator units are operated by the patients themselves, can never be completely controlled or eliminated.

My pending patent application Ser. No. 634,577 discloses a fault protection circuit for monitoring the pulse output of a stimulator to disable the stimulator's pulse generator when the current level of the output pulses increases at an excessive rate. This type circuit will detect electrode reconnect after disconnect which occurs while the stimulator is "on". Even though this fault circuit reacts very quickly to disable the stimulator, this circuit cannot eliminate altogether the electrical shock received by the patient upon electrode reconnect.

Moreover, this previous circuit used many components to sample and hold output pulses before differentiating to feed a threshold detector.

An object of this invention, therefore is to provide an improved circuit connectable to exising stimulator circuitry for detecting output load disconnect.

Another object of this invention is to provide an improved circuit for detecting excessively high load impedance.

Another object of the invention is to provide a simple and economical circuit to monitor surges in output current level.

A further object of the invention is to provide a circuit for disabling the output pulse generator within the stimulator unit when any of the undesirable conditions is detected.

An additional object of this invention is to provide the detection and control circuitry which will tolerate certain acceptable ramps normally present during stimulator adjustment.

SUMMARY OF THE INVENTION

A detection and control circuit may be connected into the output stage of a transcutaneous nerve stimulator to satisfy the objects of the invention. As such, a first monitoring circuit may be connected to measure the output or load impedance of the stimulator against a predetermined threshold. A second monitor may be connected to measure the operation of the output stage control against a second predetermined threshold. Exceeding either threshold may result in a disabling of the stimulator.

As the transcutaneous nerve stimulator may have a constant current pulse generator output component triggered by a multivibrator component its operation may be controlled by an enable/disable gate inserted therebetween and controlled by an output from either the first monitoring circuit or the second monitoring circuit.

Preferably, an impedance comparator is used to monitor the output of the constant current pulse generator. This impedance comparator may be tied to operate the enable/disable gate. Similarly, a step comparator may be connected to the adjustment potentiometer normally resident within the constant current generator. The step comparator monitors a circuit value proportional to output current. This second comparator may also be tied to operate the enable/disable gate.

A disablement signal being generated, an interlock is engaged to maintain the disablement until the circuit is reset by a specific action. An indicator light may signal the operational state of the unit.

DESCRIPTION OF THE DRAWINGS

The novel features of this invention as well as the invention itself, both as to its organization and method of operation, will best be understood from the following description taken in connection with the accompanying drawings in which like characters refer to like parts, and in which:

FIG. 1 is a block diagram of the detection and control circuit which provides the fault protection.

FIG. 2 shows the output voltage and output current wave forms of the stimulator.

FIG. 3 is a detailed block diagram of the circuitry of FIG. 1.

FIG. 4 is the schematic circuitry for the block diagram of FIG. 3.

FIG. 5 is a further block diagram.

DETAILED DESCRIPTION OF THE INVENTION

A detection and control circuit monitors the operation of a transcutaneous nerve stimulator to provide fault protection. This circuit disables the output of the transcutaneous nerve stimulator whenever the electrode impedance exceeds a preset level or whenever the output potentiometer used to adjust output current magnitude is increased by a step which exceeds the allowed maximum. In addition, the circuit will disable the output if the power source is interrupted for any reason.

Several situations which could result in uncomfortable or dangerous conditions to a patient can be protected against by this circuit. These include: the pulling of an electrode away from the skin to cause a momentary high current density as the effective electrode area is reduced in the presence of a constant current output pulse; the failure to turn off the unit before connecting electrodes to the stimulator resulting in severe shock, possibly accompanied by sudden muscle tetany; the inadvertent touching of electrodes connected to an active stimulator; and electrode lead failures creating interrupted and intermittent electrical signals to the electrodes. This latter situation could lead a patient to over adjust output power which could result in an electrical shock upon the reconnection of leads. The using of electrodes with insufficient gel or without water so as to create possible high current density "hot spots" at the electrodes; the inadvertent turning up of the output control too rapidly which could result in burn sensations and possible muscle contractions; and intermittent unit operation created by intermittent power supply connections or electrical contact failure, or improper hook-up of a unit are also among the hazardous situations intended to be protected against.

The circuit comprising this invention may be connected into the output circuit of the stimulator, FIG. 1, to disable the stimulator operation in the presence of hazard situations as indicated by excessive electrode impedance, excessive adjustment on output power or interruption of power supply.

The output circuitry of the host stimulator 10, FIG. 1, may normally include a multivibrator 11 used to drive a trigger a constant current pulse generator 13. This constant current pulse generator 13 supplies electrical excitation and stimulation pulses to a pair of electrodes 15 connected thereto; the electrodes 15 being placed in contact with a patient's skin.

The output pulse generator 13 is adjustable as to the magnitude of the current pulses generated. Adjustment is made by means of a potentiometer 17 connected into the cirucit containing the output power transistors normally contained within the pulse generator 13.

The control and monitoring function of the subject invention is incorporated into the basic stimulator output circuit 10 by introducing an "and" gate 19 into the trigger connection line 21 between the stimulator's multivibrator 11 and constant current pulse generator 13. The operation of this gate 19 is controlled to block, disable or otherwise eliminate triggering pulses to the constant current pulse generator 13 to turn off this generator 13 and to stop pulses to the electrodes 15.

The gate 19 can be driven to the disabled condition by the operation of an output impedance comparison unit 23 or a step comparison unit 25. The impedance comparison unit (i.e., voltage and current comparator) 23 operates to disable the pulse generator 13 when the output impedance exceeds a predetermined threshold. The step comparison unit 25 operates to disable the pulse generator 13 when the ouput adjustment potentiometer 17 is changed at an excessive rate. Both of these situations, excessive output impedance or excessive rate of adjustment, evidence fault conditions in stimulator operation. The output of each comparator 23, 25 is connected via "nor-gate" 27 to the and-gate 19.

The pair of electrodes 15 normally connected to the output of constant current generator 13 are applied to the skin of a patient to complete an electrical circuit. With these electrodes 15 driven by the constant current pulse, the output performance of the device can be monitored by a plot of output voltage vs time and a plot output current vs time. By driving the electrodes 15 with a constant current pulse, an output voltage response similar to the plot 29 shown in FIG. 2 is obtained. The current output pulse 31 whose current magnitude is constant for each pulse generated is also plotted in the FIG. 2. The voltage pulse 29 comprises an initial step function, V initial, coincident with the leading edge of the current pulse, followed by an exponential rise to a V final, followed by a decay being initiated coincident with the tailing edge of the current pulse. If instantaneous output impedance, V/I, were to be plotted for a given pulse duration, it would describe a shape similar to the voltage response 29. Although an impedance plot will vary greatly with electrode area, the pressure applied to the electrode, the type of electrode, etc., initial impedance, V/I, occurring coincident with the leading edge of each current pulse has been found to be relatively constant for the various electrode areas and types. Extremely small electrode areas or a dry electrode-skin interface will affect impedance, however.

As any stimulator incorporating the detection and control circuit of the instant invention should be able to operate universally with a variety of electrodes, operating parameters of the detection and control circuit, i.e., instantaneous impedance threshold should be chosen to accommodate acceptable stimulator operation and to be the best measure of electrode conditions.

The impedance (voltage and current) comparison unit 23 and step comparison unit 25 of FIG. 1 can be implemented as shown in the block diagram, FIG. 3. FIG. 3 illustrates a more detailed implementation of comparison unit 23 and step comparison unit 25. The output from the constant current pulse generator 13 is connected to the pair of electrodes 15 with the positive terminal connected to one electrode 15 and the negative terminal connected to the other. The electrode impedance, Ze, is developed across the generator 13 output terminals. This electrode impedance, Ze, includes the vector sum of the electrode's component impedances, electrode-skin interface impedance and skin and muscle impedances embodied in the bio-electrical connection. The negative terminal of the pulse generator 13 is connected to ground.

A resistor 33, FIG. 3, is connected in series connection between the generator 13 negative terminal and one of the electrodes 15. This resistor 33 provides the voltage drop indicative of output current.

Connected to a point between the indicating resistor 33 and its connected electrode 15 is an adder 35, FIG. 3. Adder 35 takes the voltage developed across the indicating resistor 33 and adds a fixed voltage, $\gamma$, before feeding a scaler 37. The scaler 37 scales the voltage sum provided by the adder 35 by a factor $K_1$.

A second scaler 39, FIG. 3, is tied to a point between the generator 13 positive terminal and its connected electrode 15. This scaler 39 senses the voltage developed across the generator's output terminals. This voltage, which is equal to the voltage drop across the electrode impedance plus the drop across the indicating resistor 33, is scaled by a factor $K_2$.

The output of the $K_2$ scaler 39 is fed to a high pass filter 41 which in turn feeds the negative input of a type LM339 comparator component 43. The positive input of comparator 43 is tied to the output of the $K_1$ scaler 37.

A "nand" gate 45 tied to the output of the comparator 43. The output of this nand-gate 45 is tied to the "set" terminal of a flip-flop 47.

The flip-flop 47, FIG. 3, is "reset" by a connection to the power-on switch 48 of the stimulator. Flip-flop 47 has its input tied to a logic "0" and its output tied to an input of the "and"-gate 19. The and-gate 19, as discussed above, is connected serially into the multivibrator 11 trigger line to the pulse generator 13. As stated above, an output from the multivibrator 11 is tied to an input terminal of the and-gate 19.

The parameters for the impedance comparison unit 23 part of the circuit have been designed so that whenever the condition:

$$Z \text{ initial} < Z \text{ max}$$

is violated, the comparator component 43 output goes "low", the nand-gate 45 output goes "high" and the flip-flop 47 output goes "high" to disable and-gate 19 and disable the constant current pulse generator. The condition of these components remain until a reset operation is performed. The high pass filter 41 is provided so that the initial portion of each pulse is The peak signal used for the voltage input to the comparator 43.

Adjustment potentiometer 17, which forms the controller regulating current amplitude of the pulses generated by the generator 13, has its wiper also connected to the step comparator 25 of FIG. 1. This circuitry is shown in greater detail by FIG. 3.

The wiper of the potentiometer 17, FIG. 3, is connected to a $K_3$ scaler 49 which in turn is connected to a low pass filter 51. The output of the low pass filter 51 is connected to the positive input of a second comparator 53.

A substractor 55, FIG. 3, also takes the voltage developed at the wiper of the potentiometer 17 and subtracts a fixed voltage before feeding a scaler 57. Scaler 57 scales the voltage difference provided by the subtractor 55 by a factor $K_3$. The output of the scaler 57 is connected to the negative input of the second comparator 53. The output of the second comparator 53 is tied to a second input of nand-gate 45.

This step comparator 25 is designed to monitor the output current amplitude. Output current amplitude is approximately proportional to the output potentiometer's 17 d.c. voltage. At steady state, the voltage at the positive input of the comparator 53 will exceed the voltage at the negative input. However, when the output potentiometer 17 is stepped by an amount (rate) greater than $\sigma$, the negative input will exceed the positive input, and the output of the comparator 53 will go low, setting the disable flip-flop 47 through nand-gate 45 and turning off the pulse generator 13.

The comparator 53 is also used to regulate pulse generator 13 operation in the presence of intermittent power supply connections. Disconnection and reconnection of power supply voltage will cause a voltage surge on the adjustment potentiometer 17 wiper which is treated identically to stepping the potentiometer 17 by a rate greater than $\sigma$.

An indicator light 59 may be included in the circuit, FIG. 3, to indicate when the pulse generator 13 has been disabled by the detection and control circuit. This light 59 can be connected to an output of the flip-flop 47 via a buffer amplifier 61.

The circuit described above is able to efficiently monitor output operations of a transcutaneous stimulator. By looking at output impedance and not just output current, the present invention is readily able to determine electrode separation. Circuit values can be chosen to sample the leading edge of each output voltage pulse and thus sample load impedance within the first few microseconds of each pulse. An immediate disconnect is possible which eliminates the sting and burn due to electrode power surges.

The present invention looks at the voltage from the output adjustment. This circuit also monitors for excessive rate of change (slope) in output current level as did my previous invention referenced above. However, the present circuit performs this function by monitoring what is essentially a d.c. level at the adjustment potentiometer 17 instead of the pulse train or a.c. output of the stimulator. Simpler circuit design, which provides for a more reliable circuit, is therefore able to be utilized to perform a task similar to my earlier invention.

The embodiment described as to FIG. 3 presents a general implementation of the invention. FIG. 4 shows one of many specific schematics of the circuit in which the invention may be embodied.

The multivibrator 11 of FIG. 1 is implemented by a mono-stable multivibrator, FIG. 4 driven by an astable mulitivibrator. An operational amplifier 63 has its positive terminal tied through 100 kilo ohm resistor 65 to supply voltage VCC. The negative input to amplifier 63 is tied through a 0.1 micro farad capacitor 67 to ground. Amplifier 63 includes a resistance feedback including an 82 k resistor 69 and a 1 M variable resistor 71. A 100 k resistor 73 connects the output of amplifier 63 to its positive input terminal. A 100 k resistor 75 is tied between amplifier 63 positive input and ground. The output terminal of amplifier 63 is connected to the negative input of a second amplifier 77 via a variable 1 M resistor 79 and 120 k resistor 81. This negative input to amplifier 77 is also tied to ground via a 200 pf capacitor 83. The positive input to amplifier 77 is tied to the positive input of amplifier 63. A resistance feedback loop from the output to the positive input of amplifier 77 includes a 1 M resistor 85. The output of the second amplifier 77 is tied to one input of nand-gate 87. This nand-gate 87 input is also tied to the supply voltage VCC through a 10 k resistor 89. The output from aplifier 63 is tied to the second input of the nand-gate 87.

Nand-gate 87, FIG. 4, along with a diode circuit form the and-gate 19 of FIG. 1. The diode circuit consists of three diodes 91, 93, 95, each being a 1N914 type. The first diode 91 is connected to the output of nand-gate 87 with its polarity for permitting current flow out of the nand-gate 87. A second diode 93 is also connected to the output of nand-gate 87 with a similar polarity. The third diode 95 is tied to the free end of the diode 93 in a reverse polarity position.

The constant current pulse generator 13 of FIG. 1 is implemented by a 33 k resistor 97, FIG. 4 tied to the junction of the second diode 93 and the third diode 95 of the and-gate 19 above. The other end of the resistor 97 is tied to the base of a 2N2222 type transistor 99. A 100 k resistor 101 ties the base of the transistor 99 to ground. The emitter of transistor 99 is also tied to ground. The collector of the transistor 99 is connected to the base of another type 2N2222 transistor 102. The collector of transistor 102 is connected to the supply voltage Vt and the emitter to ground. The base of transistor 103 is biased by supply voltage Vt through a 1 k resistor 105. Also biasing the base of the transistor 103 is the collector of transistor 102. The potentiometer 17 discussed above in respect to FIG. 3 is a 2 k variable resistor tied to supply voltage of the constant current pulse generator 13 of FIG. 1, on one end and to ground through a 1N914 type diode 107 on the other end. The wiper arm on the potentiometer 17 is connected to the base of transistor 102 through a resistor 109. The value of the resistor 109 is arbitrary as to governing the operating parameters of the circuit. The emitter of the transistor 103 is tied to supply voltage Vt, while the collector is connected to the primary of a transformer 111. A 1N4001 type diode 113 is connected across the primary winding of transformer 111 from the collector of transistor 103 to ground. The secondary coil of the transformer 111 is grounded to provide a reference for the output voltage and current signals.

A pair of electrodes 15, FIG. 4, is connected across the transformer 111 secondary winding, with a first electrode 15 being connected to the positive end and a second electrode 115 (symbolized by a resistance indicative of the impedance thereof) being connected to the grounded or neutral pin by means of a resistance 33.

Connected in series between the transformer 111 secondary winding neutral pin and the electrode connected thereto is a 100 ohm indicating resistor 33, FIG. 4. Tied to the common point between the indicating resistor 33 and the common or neutral electrode 15 is a 100 k resistor 115. Another 100 k resistor 117 is connected to the free end of the resistor 115. Tied between the free end of the resistor 117 and ground, in forward polarity, is the diode 107. The positive input terminal of a comparator 43 is tied to the juncture between resistor 115 and 117. This positive input terminal to the comparator 43 is also connected to the free end of the first diode 91. The negative input terminal to the comparator 43 is tied to the positive terminal of the transformer 111 secondary through a 220 pf capacitor 121 and a 100 k resistor 123, with the 100 k resistor 123 being connected immediately to the negative input of the comparator 43. Tied from the jointure of the capacitor 121 and the resistor 123 to ground, in reverse polarity, is a FD400 type diode 125. A 3.9 k resistor 127 connects the negative input terminal of the comparator 43 to ground.

The resistors 115, 117, FIG. 4, described above form the K1 scaler 37, FIG. 3. These resistors 115, 117 in combination with the connection of the diode 107 establish an offset which provides the function of the adder 35, FIG. 3. The resistors 123 and 127, FIG. 4, provide the K2 scaler 39, FIG. 3, while the capacitor 121 in combination with the resistors 127 and 123 establish the high pass filter 41 of FIG. 3.

The wiper of the potentiometer 17 is also connected to a 100 k resistor 129, FIG. 4. Connected between the other end of the resistor 129 and ground, in parallel, is a 1 microfarad capacitor 131 and a 100 k resistor 133. The resistors 129, 133 form the K3 scaler 49 while the resistors 129, 133 and capacitor 131 form the low pass filter 51 of FIG. 3.

Also connected to the wiper of the potentiometer 17, FIG. 4, in series connection, is a 1N914 type diode 134 and a 100 k resistor 135. Connected from the resistor 135 to ground is a 100 k resistor 137. The diode 134 being connected in forward polarity produces a voltage drop and provides the subtractor 55 function. The combination of the resistors 135, 137 provides the K3 scaler 57 function of FIG. 3. A comparator component 53 has its negative input tied to the juncture of the resistors 135, 137, while its positive input terminal is connected to the juncture of the resistors 129, 133.

The outputs of the comparators 43 and 53, FIG. 4, are tied together. This connection forms the hard wire equivalent of the nand-gate 45. The nand function being implemented because of reversal of polarity through the comparators 43, 53.

The outputs of the comparators 43, 53, FIG. 4, are connect to the input of flip-flop 47. Flip-flop 47 is implemented by a pair of 4011 nand-gates connected in standard configuration. The output from the comparators 43, 53 is tied to an input of the first nand-gate 139. This input is also tied to the supply voltage Vcc through a 100 k resistor 141. The output of the nand-gate 139 is tied to an input of the second nand-gate 143, while the output of the second nand-gate 143 is tied to a second input to the first nand-gate 139. The output of the first nand-gate 139 forms the "Q" output of the flip-flop 47. This terminal is tied to the free end of the third diode 95 forming the nand-gate 19. The output of the second nand-gate 143 forms the complementary or "Q̄" output of the flip-flop 47 and is tied to a 4011 type buffer amplifier 61. The output of the buffer amplifier 61 feeds the base of a 2N2222 type driver transistor 145, with the emitter of this transistor 145 being connected to a light emitting diode indicator 59a via a 100 ohm resistor 147. The collector of the driver transistor 145 is connected to the supply voltage Vcc. Connected to a second input of the nand-gate 143 is the power-on switch 48. Included is the series connection of the switch 48, a 100 k resistor 149 and a 1M resistor 151 from the supply voltage Vcc to ground. Connected across the resistor 151 to ground is a 1 microfarad capacitor 153. The voltage side of the capacitor 153 is tied to the second input of the nand-gate 143. The unit may be powered with a dc storage battery which provides supply voltage through 1N4001 type diodes 155 and 157. Connected across the diodes to ground are capacitors 159, 161. These capacitors can be of 275 microfarad and 50 microfarad values, respectively, and provide noise shunting paths for extraneous ac signals.

Many changes can be made in the above-described apparatus and many different embodiments can be made without departing from the scope thereof. Each of the components incorporated in the device may have alternate designs. As way of illustration, step comparison unit 25 described above in detail during the discussion of FIG. 3 can have an alternate configuration FIG. 5 incorporating a high pass filter 171 (differentiator) instead of the low pass filter 51 (integrator). In this latter embodiment, the step comparison unit 25 may be implemented, FIG. 5, as follows. The wiper of the output potentiometer 17 is connected to a $K_5$ scaler component 173. The output of this scaler 173 is connected to the negative input of the comparator 53 via a high pass filter 171. The positive input of the comparator 53 is tied to supply voltage (V+). This alternate circuit configuration performs an equivalent function.

Additionally, a scaler component 173 can be summed into the high pass filter 171 from a pulse width potentiometer resident within output generator 13. This would operate to disable the output generator 13 when this pulse width potentiometer is increased at an excessive rate. Similarly, any other adjustments available within the output generator 13 could be monitored by tying each of the high pass filter 171 via a respective scaler component. In this manner any undesirable operation of any adjustment within the generator 13 can be monitored to disable the operation of the generator. It is intended that all matter contained herein and shown in the accompanying drawings be interpreted as illustrative and not in the limiting sense.

What is claimed:

1. An improved fault protection circuit for a medical stimulator, said stimulator having a power on/off switch and triggered output pulse generating circuit with an amplitude adjustment, said output pulse circuit being connected to an electrode load comprising:
    means for monitoring the output load impedance connected to said pulse generating circuit;
    means connected to said impedance monitoring means for disabling said generating circuitry upon the detection of an excessive impedance value; and
    means for monitoring the rate of change in the magnitude of the output current from said pulse generating circuit, said output current monitoring means being connected to operate said disabling means upon the detection of an excessive rate of change in said output current magnitude, wherein said impedance monitoring means includes an impedance comparator connected to the output of said pulse generating circuitry and wherein said pulse generator disabling means includes a gate in the input trigger to said pulse generating circuitry, said gate being conditioned by a signal from said impedance comparator.

2. The circuit of claim 1 wherein said output current rate of change monitoring means includes a step comparator connected to said pulse generating circuit amplitude adjustment, said step comparator being connected to condition said pulse generator input trigger gate.

3. An improved fault protection circuit for a medical stimulator, said stimulator having a power on/off switch and triggered output pulse generating circuit with an amplitude adjustment said output pulse circuit being connected to an electrode load comprising:

means for monitoring the output load impedance connected to said pulse generating circuit, said impedance monitoring means including an impedance comparator connected to the output of said pulse generating circuitry;

means connected to said impedance monitoring means for disabling said generating circuitry upon the detection of an excessive impedance value; and means for monitoring the rate of change in the magnitude of the output current from said pulse generating circuit, said output current monitoring means being connected to operate said disabling means upon the detection of an excessive rate of change in said output current magnitude;

wherein said pulse generator disabling means includes a gate in the input trigger to said pulse generating circuitry, said gate being conditioned by a signal from said impedance comparator;

and wherein said output current rate of change monitoring means includes a step comparator connected to said pulse generating circuit amplitude adjustment, said step comparator being connected to condition said pulse generator input trigger gate said pulse generator disabling means input trigger gate including a nand-gate having at input from each said impedance comparator and said step comparator, and an and-gate, said and-gate being connected into the triggered line to said pulse generating circuit and being enabled by the output of said nand-gate.

4. The circuit of claim 3 wherein said impedance comparitor includes;

an indicating resistor connected in series with said load impedance, said indicating resistor being grounded at one side away from said load impedance;

means for sensing the voltage drop across said indicating resistor, said sensing means having adder and scaler functions;

means for sensing the voltage drop across the output of said pulse generating circuit, said output voltage sensing means having scaler and high pass filter functions; and a first comparitor component having a first input tied to said indicating resistor voltage sensing means and a second input tied to said pulse generator output voltage sensing means, The output of said first comparitor component being connected to an input to said nand-gate.

5. The circuit of claim 4 wherein said step comparitor includes:

a first means for sensing said amplitude adjustment output having scaler and low pass filter functions;

a second means for sensing said amplitude adjustment output having subtractor and scaler functions; and a second comparitor component having a first input tied to said first amplitude adjustment sensing means and a second input tied to said second amplitude adjustment sensing means. The output of said second comparitor component being connected to a second input of said nand-gate.

6. The circuit of claim 5 also including:

a flip-flop component, said flip-flop being set by the output of said nand-gate, being reset by the operation of said power on/off switch and having its output connected to an input of said and-gate;

an amplifier component connected to the output of said flip-flop; and an indicator light driven by said amplifier.

7. In a transcutaneous nerve stimulator having a power on/off switch and a triggerably operated output pulse generator for driving stimulating electrodes, said pulse generator including an amplitude control, a fault protection circuit for detecting undesirable conditions at the output, comprising:

means for disabling said pulse generator, said means being connected to regulate an input to said pulse generator;

means for monitoring output electrode load impedance said means being connected to the output of said pulse generator and to said disabling means; and means for monitoring the operation of said amplitude control, said means being connected to said disabling means and including a rate of change comparator, wherein said pulse generator disabling means includes means connected into the trigger line to said pulse generator for stopping trigger signals to said pulse generator and wherein said electrode load impedance monitoring means includes means for comparing the electrode load impedance to a fixed threshold value for driving said disabling means when said threshold is exceeded.

8. The circuit of claim 7 wherein said rate of change comparator compares rate of change in the amplitude of the output signal from said control to a reference rate for activating said disabling means when said reference rate is exceeded.

* * * * *

UNITED STATES PATENT AND TRADEMARK OFFICE
CERTIFICATE OF CORRECTION

PATENT NO. : 4,088,141
DATED : May 9, 1978
INVENTOR(S) : Bill Howard Niemi

It is certified that error appears in the above-identified patent and that said Letters Patent are hereby corrected as shown below:

In Column 1, line 32, "used many" should read ---uses many---
In Column 1, line 36, "exising stimulator" should read---existing stimulator---
In Column 4, line 39, "generator's output" should read
                              ---generator's 13 output---
In Column 4, line 48, "A "nand" gate 45 tied to the output of the
                     comparator 43." should read
                     ---A "nand" gate 45, Fig. 3, has one input terminal
                     thereof tied to the output of the comparator 43.---
In Column 5, line 1, "The peak signal" should read ---the peak signal---
In Column 5, line 13, "substractor" should read ---subtractor---
In Column 6, line 5, "voltage VCC" should read ---voltage $V_{CC}$---
In Column 6, line 43, "voltage Vt" should read ---voltage V+---
In Column 6, line 51, "on the other end." should read
                              ---on the other end, Fig. 4.---
In Column 8, line 9, "voltage VCC" should read ---voltage V+---
In Column 9, line 46, "triggered line" should read ---triggering line---

Signed and Sealed this

Twenty-seventh Day of February 1979

[SEAL]

Attest:

RUTH C. MASON
Attesting Officer

DONALD W. BANNER
Commissioner of Patents and Trademarks